United States Patent
Von Dem Bruch et al.

(10) Patent No.: US 10,125,085 B2
(45) Date of Patent: Nov. 13, 2018

(54) METHOD FOR PRODUCING 2-HALOGEN-ACRYLIC ACID ESTERS

(71) Applicant: SALTIGO GMBH, Leverkusen (DE)

(72) Inventors: Karsten Von Dem Bruch, Leverkusen (DE); Andreas Scherwitzki, Remscheid (DE)

(73) Assignee: Saltigo GmbH, Leverkusen (DE)

( * ) Notice: Subject to any disclaimer, the term of this patent is extended or adjusted under 35 U.S.C. 154(b) by 19 days.

(21) Appl. No.: 15/317,583

(22) PCT Filed: Jun. 17, 2015

(86) PCT No.: PCT/EP2015/063634
§ 371 (c)(1),
(2) Date: Mar. 22, 2017

(87) PCT Pub. No.: WO2015/193392
PCT Pub. Date: Dec. 23, 2015

(65) Prior Publication Data
US 2017/0197905 A1    Jul. 13, 2017

(30) Foreign Application Priority Data
Jun. 18, 2014 (EP) ..................... 14172874

(51) Int. Cl.
*C07C 51/00* (2006.01)
*C07C 69/63* (2006.01)
*C07C 67/287* (2006.01)

(52) U.S. Cl.
CPC ............ *C07C 69/63* (2013.01); *C07C 67/287* (2013.01)

(58) Field of Classification Search
CPC .................................................... C07C 67/287
USPC ........................................................ 562/603
See application file for complete search history.

(56) References Cited

U.S. PATENT DOCUMENTS 5,124,476 A * 6/1992 Gassen ................. C07C 51/097
560/213
5,319,131 A    6/1994 Heumueller et al.

FOREIGN PATENT DOCUMENTS

GB    1115287    5/1968
JP    2001172223 A2    6/2001

OTHER PUBLICATIONS

By Antolini et al. J. Chem. Soc. Perkin Trans, 1992, 1541-1544.*
Gault, Henry, et al. "Nouvelle syntheses des esters a-fluoracrliques et de leurs derives", C.R. Acad. Sc. Paris, t 268, 27 janvier 1969, Chimie Organique, pp. 354-357.
Prakash, G. K. Surya, et al. "Direct Electrophilic Monofluoromethylation", Organic Letters, 2008, vol. 10, No. 4, American Chemical Society, pp. 557-460.
REAXYS data sheet, XP002728399, Reed Elsevier Properties SA, 2014, two pages.
REAXYS data sheet, XP002728400, Reed Elsevier Properties SA, 2014, one page.
Krapcho, A. Paul, "Synthetic Applications of Dealkoxycarbonylations of Malonate Esters . . . ", Reviews, 1982, George Thieme Verlag, pp. 805-822.
Salomon, Claudio J. et al., "Recent Developments in Chemical Deprotection of Ester Functional Groups", Tetrahedron vol. 49, No. 18, 1993, Pergamon Press Ltd., pp. 3691-3748.
REAXYS data sheet, XP002728398, Reed Elsevier Properties SA, 2014, one page.
Krapcho, A. Paul, "Recent synthetic applications of the dealkoxycarbonylation reaction, Part 1 . . . ", Arkivoc 2007, Special Issue Reviews and Account, ARKAT USA, Inc., pp. 1-53.
McMurry, John, "Ester Cleavages via WN2-Type Dealkylation", Organic Reactions: 1976, pp. 187-224.
European Search Report from European Application No. 14172874, dated Aug. 14, 2014, five pages.

* cited by examiner

*Primary Examiner* — Ana Z Muresan

(57) ABSTRACT

The present invention relates to a process for preparing 2-haloacrylic esters from 2-hydroxymethyl- or 2-halomethyl- or 2-chlorosulfinyloxymethyl-2-halomalonic diesters. The invention further provides novel 2-halomethyl-2-halomalonic diesters or 2-chlorosulfinyloxymethyl-2-halomalonic diesters which can be used for preparation of the 2-haloacrylic esters.

14 Claims, No Drawings

METHOD FOR PRODUCING 2-HALOGEN-ACRYLIC ACID ESTERS

The present invention relates to a process for preparing 2-haloacrylic esters from 2-hydroxymethyl- or 2-halomethyl- or 2-chlorosulfinyloxymethyl-2-halomalonic diesters. The invention further provides novel 2-halomethyl-2-halomalonic diesters or 2-chlorosulfinyloxymethyl-2-halomalonic diesters which can be used for preparation of the 2-haloacrylic esters.

Substituted 2-haloacrylic esters, especially 2-fluoroacrylic esters, are reactants for synthesis of polymers. These can be used, for example, as plastics in optical light waveguides and as polymeric additives in medicaments.

The literature discloses various processes for preparing 2-fluoroacrylic esters.

Journal of Fluorine Chemistry, 55, 1991, p 149-162, discloses a process for preparing 2-fluoroacrylic esters by hydrolysis of α-hydroxymethyl-α-fluoromalonic esters, subsequent decarboxylation and reesterification. The process has the drawback that only low yields are obtained.

In addition, JP 2001172223 discloses preparing substituted 2-fluoroacrylic esters from 2,2-bromofluoropropionic esters. What is disadvantageous about this process is that the reactants are barely available and only low yields are obtained, and the process is consequently uneconomic.

EP 415 214 A discloses a four-stage process for preparing a 2-fluoroacrylic ester proceeding from 2,3-dichloro-1-propene. Further processes for preparing 2-fluoroacrylic acid derivatives proceeding from 3-hydroxy-2-fluoropropionates by reaction with toluenesulfonyl chloride and elimination of the tosylate formed in the presence of potassium phthalimide are known from Journal of Fluorine Chemistry, 1993, 60, p. 149-162 and from Coll. Czech. Chem. Commun., 1983, 48, p. 319-326. A common factor in the aforementioned processes is that they are undesirable for economic and safety reasons in industrial processes.

A further process for preparing 2-fluoroacrylic acid derivatives by reacting 3-hydroxy-2-fluoropropionates with dehydrating agents is known from Bull. Soc. Chem. Fr., 1975, p. 1633-1638. A drawback of this process is likewise the low product yield.

EP 249 867 A and EP 203 462 A disclose processes for preparing 2-fluoroacrylic esters in which dimethyl 2-fluoromalonate is reacted with formaldehyde in a first process step to give dimethyl 2-hydroxymethyl-2-fluoromalonate, which is converted in a second step with decarboxylation and dehydration to 2-fluoroacrylic acid. In a third step, by esterification of the 2-fluoroacrylic acid with an alcohol, the corresponding 2-fluoroacrylic esters are obtained.

It is a common factor in these processes too that they are either unsuitable for preparation of 2-haloacrylic esters for safety reasons or afford reaction yields that are too low because of an excessive number of process stages.

There was therefore still a need for a process for preparing 2-haloacrylic esters which overcomes the drawbacks of the prior art and with which substituted 2-haloacrylic esters can be prepared in an efficient manner in industrially feasible processes.

The invention therefore provides a process for preparing 2-haloacrylic esters of the formula (IV)

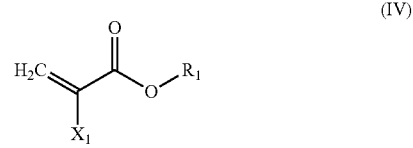

in which
$R_1$ is $C_1$-$C_{15}$-alkyl, preferably $C_1$-$C_6$-alkyl, or $C_3$-$C_6$-cycloalkyl or $C_6$-$C_{24}$-aryl and
$X_1$ is fluorine, chlorine or bromine, preferably fluorine, comprising the step of
a) reacting compounds of the formula (II)

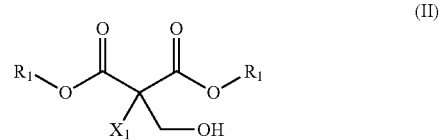

and/or compounds of the formula (III)

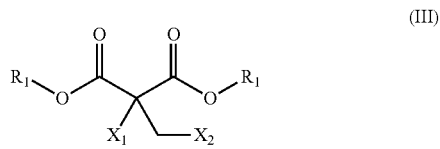

in each of which $R_1$ and $X_1$ have the definition given for formula (IV) and the two $R_1$ radicals are identical or different, preferably identical,
and where $X_2$ in formula (III) is fluorine, chlorine, chlorosulfinyloxy or bromine,
in the presence of base to give compounds of the formula (IV).

The invention further provides a process for preparing 2-haloacrylic esters of the formula (IV)

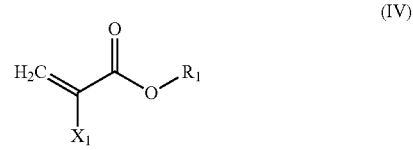

in which
$R_1$ is $C_1$-$C_{15}$-alkyl, preferably $C_1$-$C_6$-alkyl, $C_3$-$C_6$-cycloalkyl or $C_6$-$C_{24}$-aryl and
$X_1$ is fluorine, chlorine or bromine, preferably fluorine, comprising the step of
a) reacting compounds of the formula (II)

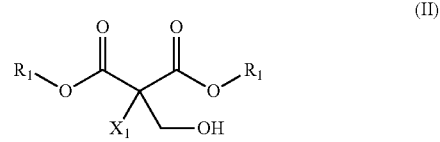

and/or compounds of the formula (III)

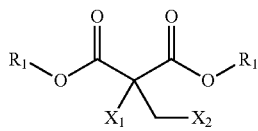

(III)

in each of which $R_1$ and $X_1$ have the definition given for formula (IV) and the two $R_1$ radicals are identical or different, preferably identical, and where $X_2$ in formula (III) is fluorine, chlorine or bromine, preferably chlorine or bromine, in the presence of base to give compounds of the formula (IV).

In the presence of base, the compounds of the formula (IV) are obtained from the compounds of the formula (II) with elimination of carbon dioxide and alcohol ($R_1$OH).

In the presence of base, the compounds of the formula (IV) are obtained from the compounds of the formula (III) with elimination of carbon dioxide and methyl halide ($CH_3X_2$).

In a further embodiment, the compounds of the formula (IV) are obtained from the compounds of the formula (III) when $X_2$=chlorosulfinyloxy, with elimination of carbon dioxide, sulfur dioxide and methyl chloride. Chlorosulfinyloxy is understood to mean the —O—SO—Cl radical.

$R_1$ in the formulae (I) to (IV) specified may, for example, be $C_1$-$C_{15}$-alkyl, $C_1$-$C_6$-alkyl, $C_3$-$C_6$-cycloalkyl or $C_6$-$C_{24}$-aryl. Preferably, $R_1$ is methyl, ethyl, n-propyl, i-propyl, n-, i-, s- or t-butyl, n-pentyl or n-hexyl, especially methyl or ethyl. More preferably, $R_1$ is methyl.

$X_1$ in the formulae (I) to (IV) specified is fluorine, chlorine or bromine. More preferably, $X_1$ is fluorine.

In one embodiment, $X_2$ in the formulae (I) to (IV) specified is chlorine or bromine. More preferably, $X_2$ is chlorine. In a further embodiment, $X_2$ in the formulae (I) to (IV) specified is fluorine, chlorine, chlorosulfinyloxy or bromine.

Particularly preferred compounds of the formula (IV) are methyl 2-fluoroacrylate and ethyl 2-fluoroacrylate, further preference being given to methyl 2-fluoroacrylate.

Particularly preferred compounds of the formula (II) are dimethyl 2-fluoro-2-hydroxymethylmalonate and diethyl 2-fluoro-2-hydroxymethylmalonate, further preference being given to dimethyl 2-fluoro-2-hydroxymethylmalonate.

Particularly preferred compounds of the formula (III) are dimethyl 2-fluoro-2-chloromethylmalonate and diethyl 2-fluoro-2-chloromethylmalonate, further preference being given to dimethyl 2-fluoro-2-chloromethylmalonate. Additionally particularly preferred compounds of the formula (III) are diethyl 2-fluoro-2-chlorosulfinyloxymethylmalonate and dimethyl 2-fluoro-2-chlorosulfinyloxymethylmalonate.

The preparation of the compounds of the formula (II) used as reactant through hydroxymethylation of dialkyl 2-halomalonates of the formula (I) with formaldehyde is common knowledge from EP 249 867 A and EP 203 462 A. The compounds of the formula (I)

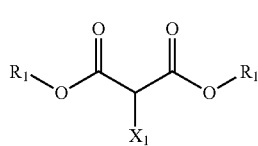

(I)

in which $R_1$ and $X_1$ have the definitions given above are likewise known and can be prepared by known processes (for example from the corresponding dialkyl malonates by halogenation or from dialkyl 2-chloromalonates by halogen exchange).

The compounds of the formula (III) used as reactants can be prepared by reacting compounds of the formula (II) with a halogenating agent.

Halogenating agents such as fluorinating, chlorinating or brominating agents are used. Halogenating agents include, for example, thionyl chloride, thionyl bromide, phosphorus trichloride, phosphorus tribromide, sulfonyl chloride, sulfonyl bromide and hydrogen halides such as hydrogen fluoride, chloride or bromide. A particularly preferred halogenating/chlorinating agent is thionyl chloride.

The halogenation process can be conducted in the presence or absence of a solvent.

Suitable solvents for the halogenation include, for example, hydrochlorocarbons, for example methylene chloride, chloroform, carbon tetrachloride, aromatic, optionally chlorinated hydrocarbons, for example toluene, xylene, chlorobenzene, 1,2-dichlorobenzene, 1,3-dichlorobenzene and 1,4-dichlorobenzene; aliphatic hydrocarbons, for example hexane, heptane, cyclohexane and methylcyclohexane or mixtures of the aforementioned solvents.

The halogenation process can be effected in the presence or absence of a base. Suitable bases include, for example, sodium hydroxide or potassium hydroxide, sodium carbonate or potassium carbonate, sodium alkoxide or potassium alkoxide, ammonia, organic amines such as triethylamine, tributylamine or pyridine, or mixtures of the aforementioned bases.

The halogenation process can be conducted, for example, at a temperature in the range from −20° C. to 200° C., preferably at 50° C. to 90° C., or further preferably at 0° C. to 50° C., or further preferably still at 80° C. to 120° C., or further preferably still at 110° C. to 170° C.

In the reaction of the compound of the general formula (II) with thionyl chloride, the product obtained may be a 2-fluoro-2-chlorosulfinyloxymethylmalonic diester ($X_2$=O—SO—Cl). This compound is obtained, for example, in the reaction of the compound of the general formula (II) with thionyl chloride at temperatures of 0 to 50° C. The reaction of the compound of the general formula (II) with thionyl chloride in the presence of a base at relatively high temperatures, for example at temperatures of 80 to 120° C., by contrast, affords the corresponding chloromethylmalonic diester. In the absence of a base, the reaction of the compound of the general formula (II) with thionyl chloride, by contrast, affords the corresponding chloromethylmalonic diester only at higher temperatures, for example at temperatures of 110 to 170° C.

The compounds of the formula (III) used alternatively or additionally as reactant in the process of the invention are novel and are therefore also encompassed by the invention, as is the preparation thereof.

In a preferred embodiment, the reactant used in the process of the invention is the compounds of the formula (III).

The advantage over the known prior art is considered to be that the process of the invention does not proceed via the preparation of the free 2-haloacrylic acid. There is thus no additional esterification step.

According to the invention, base is used. Bases used may be organic bases, for example amines, organic metal amides, alkoxides or inorganic bases. Suitable bases especially include alkaline earth metal or alkali metal hydroxides, amides, alkoxides, carbonates, hydrogenphosphates or phosphates, for example sodium amide, lithium diethylamide, sodium methoxide, potassium tert-butoxide, sodium hydroxide, potassium hydroxide, sodium carbonate, potassium carbonate, trisodium phosphate, tripotassium phosphate, disodium hydrogenphosphate, dipotassium hydrogenphosphate, sodium dihydrogenphosphate, potassium dihydrogenphosphate. The bases used are preferably sodium hydrogencarbonate or potassium hydrogencarbonate.

The process can be conducted in the presence or absence of solvent.

Suitable solvents include, for example, ethers, amides, for example sulfones, for example sulfolane; sulfoxides, for example dimethyl sulfoxide; ethers, for example dioxane; amides, for example N,N-dimethylformamide, N,N-dimethylacetamide and N-methylpyrrolidone. A particularly preferred solvent is N-methylpyrrolidone.

The process can be conducted, for example, at a temperature in the range from 120 to 170° C., preferably at 140 to 160° C.

With the aid of the process of the invention, the preparation of 2-haloacrylic esters of the formula (IV) is possible in an advantageous manner substantially without the formation of troublesome by-products.

The 2-haloacrylic esters of the formula (IV) can be purified by methods known to those skilled in the art, for example by extraction with solvents or preferably by distillation. The further processing of the 2-haloacrylic esters of the formula (IV) from the process of the invention can alternatively be effected without further workup.

By the process according to the invention, it is possible to prepare 2-haloacrylic esters of the formula (IV) in high yields and in high purity in a technically simple and safe manner. The process of the invention does not require the handling of chemicals which require special measures because of their hazard potential and is performable even on a larger scale without a problem. It is surprising, in particular, that the process of the invention affords 2-haloacrylic esters of the formula (IV) in high yield and in high purity.

The 2-haloacrylic esters of the formula (IV) prepared in accordance with the invention are especially suitable for production of plastics and polymeric additives in medicaments.

The invention further provides dialkyl 2-halomethyl-2-halomalonates of the formula (III)

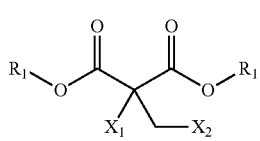
(III)

in which $R_1$, $X_1$ and $X_2$ have the definition given above.

Preferably, $R_1$ is an ethyl or methyl group, more preferably a methyl group, and $X_1$ is a fluorine atom and $X_2$ is a chlorine atom.

Dialkyl 2-halomethyl 2-halomalonates of the formula (III) were unknown to date according to the prior art. Likewise unknown according to prior art were dialkyl 2-chlorosulfinyloxymethyl-2-halomalonates of the formula (III). As described above, they can be used as starting materials for the preparation of 2-haloacrylic esters.

The invention further provides a process for preparing dialkyl 2-halomethyl-2-halomalonates of the formula (III) ($X_2$=halogen)

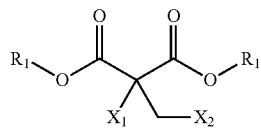
(III)

by reacting dialkyl 2-hydroxymethyl-2-halomalonates of the formula (II)

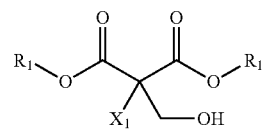
(II)

with a halogenating agent, where, in the formulae (II) and (III), $R_1$, $X_1$ and $X_2$ have the definition given above.

The invention further provides a process for preparing dialkyl 2-chlorosulfinyloxymethyl-2-halomalonates of the formula (III)

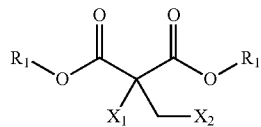
(III)

($X_2$=chlorosulfinyloxy) by reaction of dialkyl 2-hydroxymethyl-2-halomalonates of the formula (II)

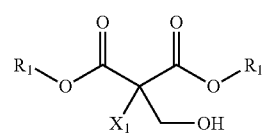
(II)

with thionyl chloride, where, in the formulae (II) and (III), $R_1$, $X_1$ and $X_2$ have the definition given above.

Preferably, $R_1$ is an ethyl or methyl group, more preferably a methyl group, and $X_1$ is a fluorine atom and $X_2$ is a chlorine atom.

The compounds of the formula (III) used as reactants can be prepared by reacting compounds of the formula (II) with a halogenating agent.

Halogenating agents used may be fluorinating, chlorinating or brominating agents. Halogenating agents include, for example, thionyl chloride, thionyl bromide, phosphorus trichloride, phosphorus tribromide, sulfuryl chloride, sulfuryl bromide and hydrogen halides such as hydrogen fluoride, chloride or bromide. A particularly preferred halogenating/chlorinating agent is thionyl chloride.

The halogenation process can be conducted in the presence or absence of a solvent.

The examples which follow serve to elucidate the invention without restricting it.

EXAMPLES

Example 1: Preparation of dimethyl 2-fluoro-2-hydroxymethylmalonate (Analogously to the Manner Described in EP-A-0203462 or EP-A-0249867).

Into a solution, prepared at room temperature, of 8 g of potassium hydrogencarbonate in 80 g of a 30% aqueous formaldehyde solution were metered, at an internal temperature of 20 to 25° C., 100 g of dimethyl 2-fluoromalonate within 1 hour. After stirring at room temperature for a further 1 hour, 112 g of product were obtained in a purity of about 88% by extraction with ethyl acetate and concentration of the extract in the form of a colorless oil which solidified rapidly at room temperature to give a colorless solid. For further purification, the product was recrystallized from toluene.

Example 2: Preparation of diethyl 2-fluoro-2-hydroxymethylmalonate (Analogously to the Manner Described in EP-A-0203462 or EP-A-0249867).

Into a solution, prepared at room temperature, of 7 g of potassium hydrogencarbonate in 70 g of a 30% aqueous formaldehyde solution were metered, after addition of 7.0 g of ethanol, 100 g of diethyl 2-fluoromalonate at an internal temperature of 20 to 25° C. within 1 hour. After stirring at room temperature for a further 3 hours, 122 g of product were obtained in a purity of about 84% by extraction with ethyl acetate and concentration of the extract in the form of a pale beige oil. For further purification, the product was recrystallized from toluene.

Example 3: Preparation of dimethyl 2-fluoro-2-chloromethylmalonate (Inventive)

To 60 g of the product from example 1 were added, at 0 to 5° C., 300 g of thionyl chloride, and the suspension that occurred as the primary product became a clear, pale beige solution after a short time. After stirring at 0 to 5° C. for a further 1 hour, 1.8 g of triethylamine were added at this temperature, and the reaction mixture was heated to reflux and heated under reflux for 48 hours. The residue that remained after concentration to dryness was taken up in 200 g of dichloromethane and the resulting solution was washed to neutrality at room temperature with 200 g of a 5% by weight aqueous sodium hydrogencarbonate solution. The organic phase was reconcentrated to dryness and the remaining residue was fractionally distilled at about 10 mbar. Nearly 50 g of a yellowish oil having a purity of >98% were obtained (about 75% of theory).

Example 4: Preparation of diethyl 2-fluoro-2-chloromethylmalonate (Inventive)

To 100 g of the product from example 2 were added, at 0 to 5° C., 400 g of thionyl chloride, and a clear brown solution formed after a short time. After stirring at 0 to 5° C. for a further 1 hour, 5.0 g of triethylamine were added at this temperature, and the reaction mixture was heated to reflux and heated under reflux for 48 hours. The residue that remained after concentration to dryness was taken up in 300 g of dichloromethane and the resulting solution was washed to neutrality at room temperature with 300 g of a 5% by weight aqueous sodium hydrogencarbonate solution. Concentrating the organic phase to dryness gave nearly 107 g of a beige oil having a purity of about 91% (about 88% of theory). For further purification, the product was fractionally distilled at 20 mbar in a distillation yield of about 80% of theory.

Example 5: Preparation of dimethyl 2-fluoro-2-chlorosulfinyloxymethylmalonate (Inventive)

60 g of the product from example 1 were melted and metered in molten form into an initial charge of 80 g of thionyl chloride at room temperature. After stirring at room temperature for a further 5 hours, the reaction mixture was concentrated to dryness under reduced pressure. The liquid phase that remained was 86 g of a beige oil having a purity of 90% (about 90% of theory).

Example 6: Preparation of dimethyl 2-fluoro-2-chloromethylmalonate from dimethyl 2-fluoro-2-chlorosulfinyloxymethylmalonate (Inventive)

68 g of the product for example 5 were fractionally distilled at 20 mbar. The distillate obtained was 27.7 g of a colorless oil having a purity of nearly 97% (about 60% of theory).

Example 7: Preparation of methyl 2-fluoroacrylate from dimethyl 2-fluoro-2-chloromethylmalonate (Inventive)

Into a mixture of 100 g of N-methylpyrrolidone, 70 g of sodium carbonate and 5 g of 2,6-di-tert-butyl-4-methylphenol were metered, at 300 mbar and 150° C., 50 g of the product from example 3 within about 4 hours. 27 g of a colorless liquid having a purity of 88% were obtained (about 93% of theory). For further purification, the product was fractionally distilled under reduced pressure with addition of 2,6-di-tert-butyl-4-methylphenol in a distillation yield of about 92% of theory.

Example 8: Preparation of methyl 2-fluoroacrylate from dimethyl 2-fluoro-2-hydroxymethylmalonate (Inventive)

A mixture, prepared at room temperature, of 50 g of N-methylpyrrolidone, 30 g of sodium carbonate, 2.5 g of 2,6-di-tert-butyl-4-methylphenol and 50 g of the product from example 1 was heated gradually to 150° C. at a reduced pressure of 300 mbar. The distillate obtained was washed at 0° C. with a 20% by weight aqueous sodium chloride solution to free it of methanol. 24 g of a colorless liquid having a purity of 96% were obtained (about 82% of theory).

For further purification, the product was fractionally distilled under reduced pressure with addition of 2,6-di-tert-butyl-4-methylphenol in a distillation yield of about 92% of theory.

Example 9: Preparation of methyl 2-fluoroacrylate from dimethyl 2-fluoro-2-chlorosulfinyloxymethylmalonate (Inventive)

Into a mixture of 40 g of N-methylpyrrolidone, 32 g of sodium carbonate and 1.4 g of 2,6-di-tert-butyl-4-methylphenol were metered, at 300 mbar and 130° C., 48.6 g of the product from example 5 within about 4 hours. The distillate obtained was washed with water at 0° C. 14.8 g of a colorless liquid having a purity of nearly 88% were obtained (about 82% of theory).

Example 10: Preparation of ethyl 2-fluoroacrylate from diethyl 2-fluoro-2-chloromethylmalonate (Inventive)

Into a mixture of 100 g of N-methylpyrrolidone, 24 g of sodium carbonate and 2.5 g of 2,6-di-tert-butyl-4-methylphenol were metered, at 300 mbar and 140° C., 50.7 g of the distilled product from example 4 within about 3 hours. The distillate obtained was 16.2 g of a colorless liquid having a purity of 80% (about 47% of theory). The crude product was freed of methanol by washing with a 20% by weight aqueous sodium chloride solution at 0° C.

What is claimed is:

1. A process for preparing 2-haloacrylic esters of the formula (IV)

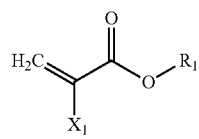

in which
R$_1$ is C$_1$-C$_{15}$-alkyl, or C$_3$-C$_6$-cycloalkyl or C$_6$-C$_{24}$-aryl and
X$_1$ is fluorine, chlorine, chlorosulfinyloxy or bromine,
the process comprising reacting compounds of the formula (II)

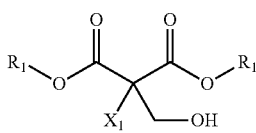

and/or compounds of the formula (III)

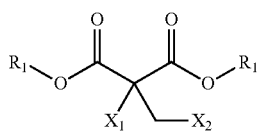

in each of which R$_1$ and X$_1$ have the definition given for formula (IV) and the two R$_1$ radicals are identical or different, and
where X$_2$ in formula (III) is fluorine, chlorine or bromine,
in the presence of base to give compounds of the formula (IV).

2. The process according to claim 1, wherein
R$_1$ is C$_1$-C$_6$-alkyl, or C$_3$-C$_6$-cycloalkyl or C$_6$-C$_{24}$-aryl, and
X$_1$ is fluorine, chlorine or bromine.

3. The process as claimed in claim 1, wherein:
R$_1$ in the formulae (I) to (IV) is C$_1$-C$_6$-alkyl, C$_3$-C$_6$-cycloalkyl or C$_6$-C$_{24}$-aryl, and
X$_1$ in the formulae (I) to (IV) is fluorine, chlorine or bromine.

4. The process as claimed in claim 1, wherein X$_2$ in the formulae (I) to (IV) is chlorine or bromine.

5. The process as claimed in claim 1, wherein X$_2$ in the formula (III) is chlorosulfinyloxy.

6. The process as claimed in claim 1, wherein the compounds of the formula (II) are prepared by hydroxymethylation of dialkyl 2-halomalonates of the formula (I) with formaldehyde

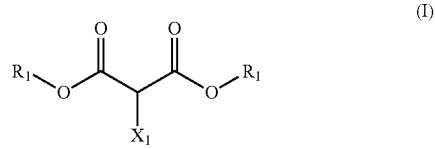

in which R$_1$ and X$_1$ have the definitions given in claim 1.

7. The process as claimed in claim 1, wherein the compounds of the formula (III) are prepared by reaction of compounds of the formula (II) with a halogenating agent.

8. The process as claimed in claim 7, wherein the halogenating agents are selected from the group consisting of thionyl chloride, thionyl bromide, phosphorus trichloride, phosphorus tribromide, sulfuryl chloride, sulfuryl bromide and hydrogen halides.

9. The process as claimed in claim 1, wherein the 2-haloacrylic esters of the formula (IV) are methyl 2-fluoroacrylate or ethyl 2-fluoroacrylate and the compounds of the formula (II) and (III) respectively are:
dimethyl 2-fluoro-2-hydroxymethylmalonate or diethyl 2-fluoro-2-hydroxymethylmalonate, and
dimethyl 2-fluoro-2-chloromethylmalonate or diethyl 2-fluoro-2-chloromethylmalonate.

10. The process as claimed in claim 1, wherein the 2-haloacrylic esters of the formula (IV) are methyl 2-fluoroacrylate or ethyl 2-fluoroacrylate prepared from compounds of the formula (III) wherein the compounds of the formula (III) are:
dimethyl 2-fluoro-2-chlorosulfinyloxymethylmalonate or diethyl 2-fluoro-2-chlorosulfinyloxymethylmalonate.

11. The process as claimed in claim 1, wherein the base is selected from organic or inorganic bases.

12. The process as claimed in claim 1, wherein the base is selected from the group consisting of alkaline earth metal or alkali metal hydroxides, amides, alkoxides, carbonates, hydrogenphosphates, phosphates, for example sodium amide, lithium diethylamide, sodium methoxide, potassium tert-butoxide, sodium hydroxide, potassium hydroxide, sodium carbonate, potassium carbonate, trisodium phosphate, tripotassium phosphate, disodium hydrogenphosphate, dipotassium hydrogenphosphate, sodium dihydrogenphosphate, potassium dihydrogenphosphate.

13. The process as claimed in claim 1, wherein the reacting is conducted in the presence of solvent.

14. The process as claimed in claim 1, wherein the reacting is conducted at a temperature of 120 to 170° C.

* * * * *